United States Patent [19]

Ohashi et al.

[11] Patent Number: 5,175,321

[45] Date of Patent: Dec. 29, 1992

[54] AMIDE DERIVATIVES AND DERMATOLOGIC PREPARATIONS CONTAINING THE SAME

[75] Inventors: Yukihiro Ohashi; Mituo Suda, both of Ichigai; Shinji Yano, Iwade; Akira Kawamata, Utsunomiya; Minehiro Okuda, Kamimikawa; Genji Imokawa, Utsunomiya, all of Japan

[73] Assignee: KAO Corporation, Tokyo, Japan

[21] Appl. No.: 524,864

[22] Filed: May 18, 1990

[30] Foreign Application Priority Data

May 19, 1989 [JP] Japan ................. 1-126461
May 19, 1989 [JP] Japan ................. 1-126462

[51] Int. Cl.$^5$ .............................. C09F 5/08
[52] U.S. Cl. ..................... 554/63; 514/844; 514/886
[58] Field of Search ........... 260/404; 514/625, 740, 514/844, 886; 554/63

[56] References Cited

FOREIGN PATENT DOCUMENTS 227994 7/1987 European Pat. Off. .
216852 9/1988 Japan .

OTHER PUBLICATIONS

Chemical Abstracts 110:945423n.

Primary Examiner—Jose G. Dees
Assistant Examiner—Deborah D. Carr
Attorney, Agent, or Firm—Birch, Stewart, Kolasch & Birch

[57] ABSTRACT

An amide derivative represented by the following general formula (I) or (II):

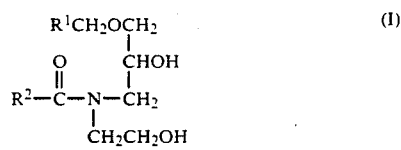

(I)

(wherein $R^1$ and $R^2$ represent each a straight-chain or branched, saturated or unsaturated hydrocarbon group provided that one of them carries 26 to 39 carbon atoms while the other carries 9 to 39 carbon atoms); or

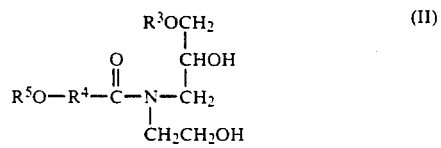
(II)

(wherein $R^3$ represents a straight-chain or branched, saturated or unsaturated hydrocarbon group carrying 10 to 40 carbon atoms; $R^4$ represents a straight-chain or branched hydrocarbon group carrying 3 to 39 carbon atoms; and $R^5$ represents a dydrogen atom, a straight-chain or branched, saturated or unsaturated hydrocarbon group carrying 10 to 40 carbon atoms or an acyl group);

and a dermatologic preparation containing the same.

5 Claims, No Drawings

AMIDE DERIVATIVES AND DERMATOLOGIC PREPARATIONS CONTAINING THE SAME

BACKGROUND OF THE INVENTION

1. Field of the Invention

This invention relates to novel amide derivatives and dermatologic preparations containing the same. More particularly, it relates to dermatologic preparations capable of essentially improving the barrier functions of the horny layer, namely, maintaining normal barrier functions and restoring damaged barrier functions.

2. Description of the Prior Art

The horny layer is located on the outermost side of the skin to covering the whole body to thereby protect the body from external irritation and invasion of foreign substances and to inhibit the evaporation of moisture contained in the body.

When these barrier functions of the horny layer are weakened for some reason, the skin frequently suffers from troubles such as inflammation or chapping.

Furthermore, it is known that poverty or deficiency of essential fatty acids (for example, arachidonic acid or linoleic acid), which is caused by prolonged intake of foods free from essential fatty acids, is accompanied by disorders in the barrier functions of the horny layer.

As a result of analyses on intercellular lipids, it has been found that the intercellular lipids of the horny layer, in particular, O-acylceramide, significantly contribute to the maintenance of the above-mentioned barrier functions of the horny layer.

It is believed, furthermore, that lipids secreted from sebaceous glands form a sebaceous membrane on the surface of the skin so as to partially make up for the barrier functions of the horny layer. Thus dermatologic preparations containing, for example, vaseline have been used in order to form a coating on the surface of the skin so as to make up for the barrier functions of the horny layer.

However known dermatologic preparations cannot essentially improve the barrier functions of the horny layer but merely form a tentative coating on the surface of the skin so as to make up for the barrier functions.

SUMMARY OF THE INVENTION

It is an object of the present invention to provide dermatologic preparations capable of maintaining the normal barrier functions of the horny layer and restoring damaged barrier functions. Namely, the dermatologic preparation of the present invention can essentially improve the barrier functions of the horny layer so as to suppress inflammation and chapping.

In order to achieve the above-mentioned object, the present inventors have conducted extensive studies. As a result, they have found out that dermatologic preparations containing novel amide derivatives represented by the following general formula (I) or (II) can essentially improve the barrier functions of the horny layer, thus completing the present invention:

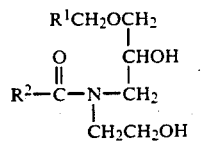

(I)

(wherein $R^1$ and $R^2$ represent each a straight-chain or branched, saturated or unsaturated hydrocarbon group provided that one of them carries 26 to 39 carbon atoms while the other carries 9 to 39 carbon atoms);

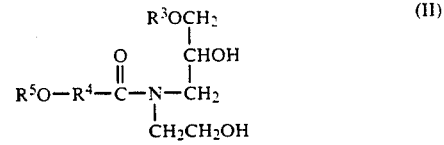

(II)

(wherein $R^3$ represents a straight-chain or branched, saturated or unsaturated hydrocarbon group carrying 10 to 40 carbon atoms; $R^4$ represents a straight-chain or branched hydrocarbon group carrying 3 to 39 carbon atoms; and $R^5$ represents a hydrogen atom, a straight-chain or branched, saturated or unsaturated hydrocarbon group carrying 10 to 40 carbon atoms or an acyl group).

Accordingly, the present invention provides a novel amide derivative represented by the above general formula (I), a novel amide derivative represented by the above general formula (II) and dermatologic preparations containing at least one of these amide derivatives.

The dermatologic preparations of the present invention containing the amide derivatives of the present invention represented by the above general formula (I) or (II) are effective in essentially improving the barrier functions of the horny layer. When applied to the skin, they can suppress inflammation and chapping.

DETAILED DESCRIPTION OF THE INVENTION

First, the amide derivative of the present invention represented by the above-mentioned general formula (I) will be described.

The amide derivative of the present invention represented by the above-mentioned general formula (I) may be prepared in accordance with a known method described in, for example, Japanese Patent Laid-Open No. 216852/1988. That is, it may be obtained according to the following reaction scheme wherein a compound (III) prepared from glycidyl ether and ethanolamine is reacted with a fatty acid lower alkyl ester in the presence of a base catalyst while distilling off the lower alcohol thus formed:

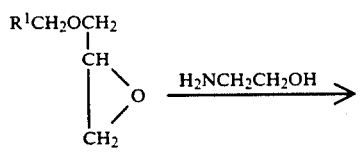

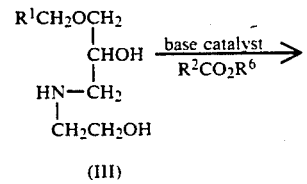

(III)

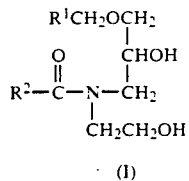

(I)

(wherein R¹ and R² are as defined above; and R⁶ represents an alkyl group carrying one to five carbon atoms).

Next, the amide derivative of the present invention represented by the above-mentioned general formula (II) will be described.

The method for preparing the amide derivative of the present invention represented by the general formula (II) is not particularly restricted. Thus it may be prepared by, for example, the following methods (1) to (3).

(1) Method for preparing an amide derivative (II-A) of the general formula (II) wherein R⁵ is a hydrogen atom:

This derivative (II-A) may be prepared in accordance with a known method described in, for example, Japanese Patent Laid-Open No. 216852/1988. According to the following reaction scheme, an amine derivative (IV) prepared from glycidyl ether and ethanolamine is reacted with a hydroxy fatty acid lower alkyl ester (V-A) or a hydroxy fatty acid lactone (VI) in the presence of a base catalyst while distilling off the lower alcohol thus formed:

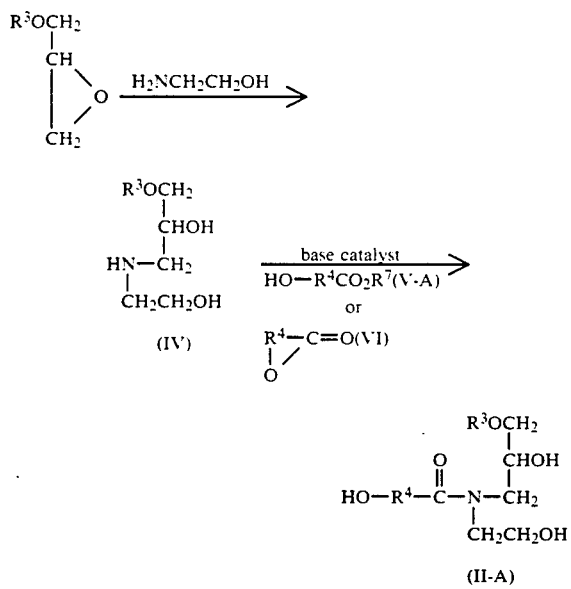

(wherein R³ and R⁴ are as defined above; and R⁷ represents an alkyl group carrying one to five carbon atoms).

(2) Method for preparing an amide derivative (II-B) of the general formula (II) wherein R⁵ is a straight-chain or branched, saturated or unsaturated hydrocarbon group carrying 10 to 40 carbon atoms:

This derivative (II-B) may be prepared in accordance with the following reaction scheme wherein a hydroxy fatty acid (V) or a hydroxy fatty acid ester (V-A) is reacted with an alkyl halide (VII) or an alkyl sulfonate (VIII) in the presence of a base to give an etherified fatty acid ester (V-B), which is then reacted with an amide derivative (IV) obtained by the above method (1) in the presence of a base catalyst while distilling off the alcohol thus formed:

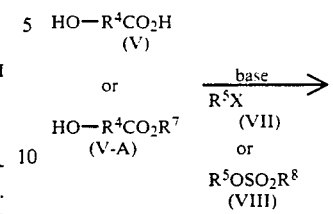

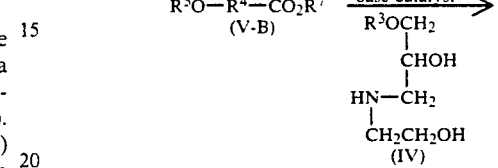

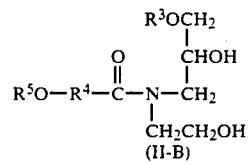

(wherein R³, R⁴ and R⁷ are as defined above; R⁵ represents a straight-chain or branched, saturated or unsaturated hydrocarbon group carrying 10 to 40 carbon atoms; R⁸ represents a methyl, phenyl or p-tolyl group; and X represents a chlorine, bromine or iodine atom).

(3) Method for preparing an amide derivative (II-C) of the general formula (II) wherein R⁵ is a straight-chain or branched, saturated or unsaturated acyl group carrying 10 to 40 carbon atoms:

This derivative (II-C) may be prepared according to the following reaction scheme wherein a hydroxy fatty acid ester (V-A) is condensed with a fatty acid (IX) in the presence of an appropriate dehydrating agent [such as

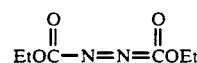

and P(C₆H₅)₃] to give an acylated fatty acid ester (V-C), which is then reacted with the amide derivative (IV) obtained by the above method (1) in the presence of a base catalyst while distilling off the alcohol thus formed:

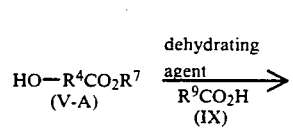

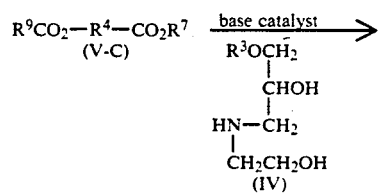

-continued

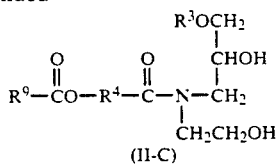

(II-C)

(wherein $R^3$, $R^4$ and $R^7$ are as defined above; and $R^9$ represents a straight-chain or branched, saturated or unsaturated hydrocarbon group carrying 9 to 39 carbon atoms).

Next, the dermatologic preparation of the present invention containing the amide derivative (I) or (II) of the present invention represented by the above general formula (I) or (II) will be described.

The content of the amide derivative (I) or (II) of the present invention in the dermatologic preparation of the present invention is not particularly restricted. In the case of an emulsion type preparation, the amide derivative (I) or (II) may be preferably contained in an amount of 0.001 to 50% (by weight, the same will apply hereinafter) based on the whole preparation. In the case of an oily preparation containing a liquid hydrocarbon such as squalane as a base, the amide derivative (I) or (II) may be preferably contained in an amount of 0.01 to 50%.

The dermatologic preparations of the present invention may be prepared by blending a base commonly used for dermatologic preparations with the amide derivative (I) or (II) of the present invention. The dermatologic preparations may be broadly classified into medicinal dermatologic preparations and cosmetics depending on the applications thereof.

Examples of the medicinal dermatologic preparations include various ointments containing medicinal ingredients. These ointments may contain either an oily base or an OW or W/O emulsion base. The oily base is not particularly restricted and examples thereof include vegetable oils, animal oils, synthetic oils, fatty acids and natural and synthetic glycerides. The medicinal ingredients are not particularly restricted and, for example, analgesics, antiinflammatory agents, antipruritic agents, bactericides, astringents, skin emollients and hormones may be used therefor, if required.

In using the dermatologic preparations of the present invention as the cosmetic, the essential ingredient, i.e., the amide derivative (I) or (II) of the present invention may be arbitrarily blended with, for example, oleaginous components, humectants, ultraviolet absorbers, alcohols, chelating agents, pH modifiers, preservatives, thickeners, colorants and perfumes commonly employed in the art.

The dermatologic preparations may be formulated into various skin cosmetics including W/O and O/W emulsions, cream, cosmetic milky lotion, cosmetic lotion, lipstick, foundation, skin cleanser, hair tonic, hair styling lotion, hair nourishment and hair growth stimulant.

Function

The function mechanism of the dermatologic preparations of the present invention containing the amide derivative (I) or (II) of the present invention represented by the above-mentioned general formula (I) or (II) has not been completely clarified in detail. It is assumed, however, that the application thereof to the skin as a dermatologic preparation might serve to reinforce the intercellular lipid membrane of the horny layer so as to improve the barrier function of the horny layer.

To further illustrate the present invention, the following Examples will be given.

EXAMPLE 1

Synthesis of N-(2-hydroxy-3-hexadecyloxypropyl)-N-2-hydroxyethyltriacontanamide (Ia) [amide derivative of the general formula (I) wherein $R^1$ is $C_{15}H_{31}$ and $R^2$ is $C_{29}H_{59}$]

(1) Synthesis of N-(2-hydroxy-3-hexadecyloxypropyl)ethanolamine (IIIa):

61.1 g (1.0 mol) of ethanolamine was introduced into a 200-ml four-necked flask equipped with a stirrer, a dropping funnel, a thermometer and a reflux condenser and heated to 60° to 70° C. under stirring. 24.3 g (0.082 mol) of hexadecyl glycidyl ether was added dropwise thereto over a period of 45 minutes. After the addition was completed, the resulting mixture was heated and stirred under the same conditions as those described above for additional two hours. Then unreacted ethanolamine was distilled off under reduced pressure (79° to 81° C./20 Torr). The residue was purified by silica gel flash column chromatography to thereby give 18.4 g of the compound (IIIa) at a yield of 63%. The data of the $^1$H-NMR of the obtained compound are as follows:

$^1$H-NMR (δ, CDCl$_3$): 0.85 (t, 3H), 1.23 (bs, 28 H), 2.6~2.8 (m, 4H), 3.1~3.9 (m, 10H)

(2) Synthesis of the amide derivative (Ia):

5.39 g (15 mmol) of the compound (IIIa) obtained in the above item (1) and 0.042 g (0.75 mmol) of KOH were introduced into a 50-ml flask equipped with a stirrer, a dropping funnel, a thermometer and a distilling tube. While stirring the mixture by heating under reduced pressure (90° C./20 Torr), 7.00 g (15 mmol) of methyl triacontanoate was added dropwise thereto over a period of 1.5 hours. After the completion of the addition, the mixture was further stirred under the same conditions as those described above for additional two hours. The crude product thus obtained was purified by silica gel flash column chromatography to thereby give 8.95 g the compound (Ia) at a yield of 75%. The melting point and IR and 1H-NMR data of the obtained compound are as follows:

m.p.: 82.2°~83.0° C.

IR: 3310.2920, 2854, 1617, 1470, 1110, 1062, 720 cm$^{-1}$ $^1$H-NMR (δ, CDCl$_2$): 0.88 (t, J=6.5 Hz, 6H), 1.01~1.73 (m, 82 H), 2.31-2.45 (m, 2H), 3.08-4.28 (m, 13 H)

EXAMPLE 2

Synthesis of N-(2-hydroxy-3-dotriacontyloxypropyl)-N-2-hydroxyethyltriacontanamide (Ib) [amide derivative of the general formula (I) wherein $R^1$ is $C_{31}H_{63}$ and $R^2$ is $C_{29}H_{59}$]

The procedure of Example 1 (1) was repeated except that the hexadecyl glycidyl ether was replaced with dotriacontyl glycidyl ether to thereby give the compound (Ib) in the form of a colorless powder at a yield of 71%. The melting point and IR and $^1$H-NMR data of the obtained compound are as follows m.p.: 88.2~88.9° C.

IR: 3316, 2920, 2854, 1617, 1467, 1107, 1059, 720 cm$^{-1}$ $^1$H-NMR (δ, CDCl$_3$): 0.88 (t, J=6.6 Hz, 6 H), 0.99~1.72 (m, 114 H), 2.25~2.45 (m, 2H), 2.95~4.28 (m, 13H).

EXAMPLE 3

Synthesis of N-(2-hydroxy-3-dotriacontyloxypropyl)-N-2-hydroxyethylhexadecanamide (Ic) [amide derivative of the general formula (I) wherein R$^1$ is C$_{31}$H$_{63}$ and R$^2$ is C$_{15}$H$_{31}$]

The procedure of Example 1 was repeated except that the hexadecyl glycidyl ether used in Example 1 (1) was replaced with dotriacontyl glycidyl ether and the methyl triacontanoate used in Example 1 (2) was replaced with methyl hexadecanoate to thereby give the compound (Ic) in the form of a colorless powder at a yield of 80%. The melting point and IR and 1H-NMR data of the obtained product are as follows:

m.p.: 62.6~64.0° C.

IR: 3304, 2920, 2854, 1617, 1467, 1056, 720 cm$^{-1}$ $^1$H-NMR (δ, CDCl$_3$): 0.88 (t, J=6.6 Hz, 6H), 0.98~1.71 (m, 86 H), 2.25~2.48 (m, 2H), 3.24~4.25 (m, 13 H).

EXAMPLE 4

The dermatologic preparations of the present invention comprising 10% of each of the amide derivatives of the present invention listed in Table 1 and 90% of squalane were prepared. Then the transepidermal water loss and percutaneous absorption of each dermatologic preparation were evaluated in the following manner. For comparison, a comparative dermatologic preparation comprising squalane alone was also evaluated. Table 1 summarizes the results.

(Test method)

Wistar male rats were fed with a feed free from essential fatty acids. Then each dermatologic preparation was applied to the shaven dorsal skin of the rat showing essential amino acid deficiency once a day for three weeks. On the next day of the completion of the application for three weeks, the following items were examined.

Each lot involved three rats.

(1) Transepidermal water loss

The dorsal skin of the rat was washed with water at 37° C. and the animal was allowed to stand in a room at 20° C. under a humidity of 45% for an hour. Then the transepidermal water loss was measured with an evaporimeter. A larger water loss means lower barrier functions of the horny layer and more serious chapping.

When the normal barrier functions are maintained, this value is smaller than 10. On the other hand, an essential fatty acid deficient rat having damaged barrier functions shows a value exceeding 35. Each value is expressed in "mean±standard deviation".

(2) Percutaneous absorption

The dorsal skin of the rat was washed with water at 37° C. Next, said skin was cut and inserted into a percutaneous absorption chamber with the epidermal side thereof directed upward. A lower receiver of the chamber was filled with a phosphate buffer equilibrated salt solution while a container on the epidermal side thereof was charged with 1 ml of a solvent containing 37 KBq of $^{14}$C-salicylic acid. After two hours, the amount of the $^{14}$C-salicylic acid penetrating into the lower receiver was determined. When the normal barrier functions are maintained, the $^{14}$C-salicylic acid scarcely penetrates after two hours. This value increases as the barrier functions are more seriously damaged. Each value is expressed in "mean±standard deviation".

TABLE 1

|  | Amide derivative | Transepidermal water loss | Percutaneous absorption |
|---|---|---|---|
| Product of Invention | compound of Ex. 1 (Ia) | 29.2 ± 6.8 | 546 ± 260 |
|  | compound of Ex. 2 (Ib) | 20.8 ± 7.2 | 778 ± 265 |
|  | compound of Ex. 3 (Ic) | 18.6 ± 4.8 | 546 ± 320 |
| Comparison | squalane alone | 35.8 ± 9.6 | 1220 ± 240 |

EXAMPLE 5

By using each of the amide derivatives of the present invention, the dermatologic preparations of the present invention as specified in Table 2 (emulsion cosmetic) were prepared. The effect of each product on improving skin chapping was evaluated in the following manner. For comparison, a dermatologic preparation free from any amide derivative of the present invention (comparative product) was evaluated in the same manner. Table 3 summarizes the results.

(Test method)

Ten female subjects aged 20 to 40 years, who suffered from chapping of the cheeks in winter, were employed. Different dermatologic preparations were applied on the right and left cheeks of the subjects once a day for three weeks. On day after completion of the application for three weeks, the following items were examined.

(1) Transepidermal water loss

The face of each subject was washed with water at 37° C. and then she was allowed to stand in a room at 20° C. under a humidity of 45% for an hour. Then the transepidermal water loss was measured with an evaporimeter. A larger water loss means lower barrier functions of the horny layer and more serious chapping. When this value exceeds 40, serious chapping is observed. When it is smaller than 10, on the other hand, scarcely any chapping is observed. Each value is expressed in "mean±standard deviation".

(2) Skin chapping score

Skin chapping was observed with the naked eye and evaluated based on the following criteria. Each score is expressed in "mean±standard deviation".

| score | Evaluation of chapping |
|---|---|
| 0 | no chapping observed. |
| 1 | slight chapping observed. |
| 2 | chapping observed. |
| 3 | somewhat serious chapping observed. |
| 4 | serious chapping observed. |

TABLE 2

| (% by weight) | Invention products | Comparative product |
|---|---|---|
| methyl-branched isostearyl glyceryl ether | 2.0 | 2.0 |
| 2-octyldodecyl myristate | 10.0 | 10.0 |
| vaseline | 3.0 | 3.0 |
| squalane | 5.0 | 5.0 |

TABLE 2-continued

| | (% by weight) | |
|---|---|---|
| | Invention products | Comparative product |
| tocopherol acetate | 0.5 | 0.5 |
| amide derivative (refer to Table 3) | 1.0 | — |
| water | the balance | the balance |

TABLE 3

| | Amide derivative | Transepidermal water loss | Skin chapping score |
|---|---|---|---|
| Invention product | compound of Ex. 1 (Ia) | 24.3 ± 5.3 | 1.5 ± 0.3 |
| | compound of Ex. 2 (Ib) | 19.8 ± 6.4 | 1.3 ± 0.4 |
| | compound of Ex. 3 (Ic) | 17.6 ± 4.8 | 0.9 ± 0.3 |
| Comparative product | — | 28.6 ± 9.8 | 2.4 ± 0.7 |

EXAMPLE 6

Synthesis of N-(2-hydroxy-3-hexadecyloxypropyl)-N-2-hydroxyethyl-12-hydroxyoctadecanamide (II-Aa) [amide derivative of the general formula (II) wherein $R^3$ is $C_{16}H_{33}$ and $R^5O-R^4$ is

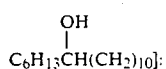

$$\begin{array}{c} OH \\ | \\ C_6H_{13}CH(CH_2)_{10}]: \end{array}$$

(1) Synthesis of N-(2-hydroxy-3-hexadecyloxypropyl)ethanolamine (IVa):

61.1 g (1.0 mol) of ethanolamine was introduced into a 200-ml four-necked flask equipped with a stirrer, a dropping funnel, a thermometer and a reflux condenser and heated to 60° to 70° C. under stirring. 24.3 g (0.082 mol) of hexadecyl glycidyl ether was added dropwise thereto over a period of 45 minutes. After the completion of the addition, the resulting mixture was stirred by heating under the same conditions as those described above for additional two hours. Then unreacted ethanolamine was distilled off under reduced pressure (79° to 81° C./20 Torr). The residue was purified by silica gel flash column chromatography to thereby give 18.4 g of the compound (IVa) at a yield of 63%. The 1H-NMR data of the obtained compound are as follows:

$^1$H-NMR (δ, CDCl$_3$): 0.85 (t, 3H), 1.23 (bs, 28 H), 2.6-2.8 (m, 4H), 3.1~3.9 (m, 10H)

(2) Synthesis of amide derivative (II-Aa):

17.3 g (48 mmol) of the compound (IVa) obtained in the above item (1) and 0.14 g (2.5 mmol) of KOH were introduced into a 100-ml flask equipped with a stirrer, a dropping funnel, a thermometer and a distilling tube. While stirring the mixture by heating under reduced pressure (80° C./20 Torr), 15.1 g (48 mmol) of methyl 12-hydroxyoctadecanoate was added dropwise thereto over a period of an hour. After the completion of the addition, the mixture was further stirred under the same conditions as those described above for additional one hour. The crude product thus obtained was purified by silica gel flash column chromatography to thereby give 23.0 g the compound (II-Aa) at a yield of 74%. The melting point and IR and 1H-HMR data of the obtained compound are as follows:

m.p.: 70.8°~71.3° C. IR: 3352, 2926, 2854, 1617, 1473, 1122, 1077 cm$^{-1}$ $^1$H-NMR (δ, CDCl$_3$): 0.88 (t, J=6.3 Hz, 6H), 1.12~1.82 (m, 56H), 2.24~2.51 (m, 2H), 3.23~4.30 (m, 15 H).

EXAMPLE 7

Synthesis of N-(2-hydroxy-3-hexadecyloxypropyl)-N-2-hydroxyethyl-16-hydroxyhexadecanamide (II-Ab) [amide derivative of the general formula (II) wherein $R^3$ is $C_{16}H_{33}$ and $R^5O R^4$ is $HO(CH_2)_{15}$]

The amine (IVa) obtained in Example 1 (1) was reacted with methyl 16-hydroxyhexadecanoate in the same manner as the one described in Example 1 (2) to thereby give the compound in the form of a colorless powder at a yield of 75%. The melting point and IR and 1H-NMR data of the obtained product are as follows:

m.p.: 80.6°~81.5° C.

IR: 3370, 2920, 2854, 1626, 1596, 1473, 1131, 1062, 723 cm$^{-1}$ $^1$H-NMR (δ, CDCl$_3$): 0.88 (t, J=6.6 Hz, 3H), 0.96~1.80 (m, 54H), 2.30~2.48 (m, 2H), 3.24~4.17 (m, 15 H).

EXAMPLE 8

Synthesis of N-(2-hydroxy-3-hexadecyloxypropyl)-N-2-hydroxyethyl-16-(9Z,12Z-octadecadienyloxy)hexadecanamide (II-Ba) [amide derivative of the general formula (II) wherein $R^3$ is $C_{16}H_{33}$ and $R^5O-R^4$ is

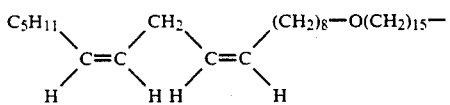

(1) Synthesis of methyl 16-(9Z,12Z-octadecadienyloxy)hexadecanoate (V-Ba):

2.72 g (10 mmol) of 16-hydroxyhexadecanoic acid, 50 ml of dry tetrahydrofuran, 5 ml of dry hexamethylphosphoric triamide and 0.24 g (10 mmol) of sodium hydride were introduced into a 300-ml four-necked flask equipped with a stirrer, a dropping funnel, a thermometer and a reflux condenser and stirred at room temperature under a nitrogen gas stream for 30 minutes. Next, the mixture was cooled to −70° C. and 6.25 ml (10 mmol) of a 1.6 N solution of butyllithium in hexane was added thereto. The resulting mixture was heated to room temperature over a period of 30 minutes and 0.24 g (10 mmol) of sodium hydride was added thereto. The mixture was further stirred at room temperature for additional 30 minutes. Then 9.25 g (22 mmol) of 9Z,12Z-octadecadienyl p-toluenesulfonate was added dropwise thereto and the mixture was heated to 65° C. under stirring for 18 hours. Then 150 ml of dry methanol was added to the reaction mixture and the resulting mixture was further stirred at 65° C. for an hour. The reaction mixture was cooled to room temperature and the excess alkali was neutralized with an aqueous solution of ammonium chloride. The reaction mixture was extracted with toluene and the solvent was distilled off under reduced pressure. Then the residue was purified by silica gel flash column chromatography to thereby give 0.72 g of the compound (V-Ba) at a yield of 13.5%.

(2) Synthesis of amide derivative (II-Ba):

The compound (V-Ba) obtained in the above item (1) was reacted with the amine (IVa) obtained in Example 1 (1) in the same manner as the one described in Example 1 (2). Thus the compound (II-Ba) was obtained in the form of a colorless powder at a yield of 71%. The melting point and IR and 1H-NMR data of the obtained compound are as follows:

m.p.: 63.0° ~ 64.3° C. IR: 3304, 2920, 2854, 1614, 1467, 1116, 1062, 720 cm$^{-1}$ $^1$H-NMR ($\delta$, CDCl$_3$): 0.80~0.95 (m, 6H), 0.95~1.70 (m, 72 H), 1.95~2.12 (m, 4H), 2.39 (t, J=7.7 Hz, 2), 2.77 (bt, J=5.7 Hz, 2 H), 3.39 (t, J=6.6 Hz, 4H), 3.23~4.23 (m, 13 H), 5.24~5.44 (m, 4H).

EXAMPLE 9

Synthesis of N-(2-hydroxy-3-hexadecyloxypropyl)-N-2-hydroxyethyl-16-(9Z,12Z-octadecadienoyloxy)hexadecanamide (II-Ca) [amide derivative of the general formula (II) wherein R$^3$ is C$_{16}$H$_{33}$ and R$^5$O-R$^4$ is

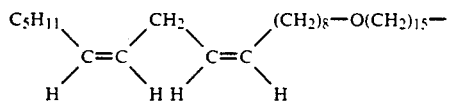

(1) Synthesis of methyl 16-(9Z,12Z-octadecadienoyloxy)hexadecanoate (V-Ca):

4.30 g (15 mmol) of methyl 16-hydroxyhexadecanoate, 8.41 g (13 mmol) of linoleic acid, 7.87 g (30 mmol) of triphenylphosphine and 100 ml of tetrahydrofuran were fed into a 300-ml flask equipped with a stirrer, a dropping funnel and a thermometer and 5.22 g (30 mmol) of diethyl azodicarboxylate was added dropwise thereto at room temperature under stirring over a period of an hour. After the completion of the addition, the mixture was further stirred at room temperature for four hours. After distilling off the solvent under reduced pressure, the residue was purified by silica gel flash column chromatography to thereby give 6.76 g of the compound (V-Ca) at a yield of 82%.

(2) Synthesis of amide derivative (II-Ca):

2.74 g (5 mmol) of the compound (V-Ca) obtained in the above item (1), 1.80 g (5 mol) of the amine (IVa) obtained in Example 1 (1) and 0.28 g (0.25 mmol) of potassium tert-butoxide were fed into a 50-ml flask equipped with a stirrer, a dropping funnel, a thermometer and a distilling tube. Then the mixture was stirred by heating under reduced pressure (80° C./20 Torr) for 30 minutes. The crude product thus obtained was purified by silica gel column chromatography and gel chromatography to thereby five 1.65 g of the compound (II-Ca) at a yield of 38%. The melting point and IR, $^1$H-NMR and MS data of the obtained compound are as follows:
m.p.: 58.2°~58.9° C.
IR: 3304, 2920, 2856, 1734, 1612, 1464, 1440, 1216, 1166, 1108, 756, 720 cm$^{-1}$ $^1$H-NMR ($\delta$, CDCl$_3$): 0.80~1.00 (m, 6H), 1.00~1.73 (m, 60H), 1.95~2.16 (m, 4H), 2.28 (t, J=7.5 Hz, 2H), 2.39 (bt, J=7.7 Hz, 2 H), 2.77 (bt, J=5.9 Hz, 2H)., 3.23~4.25 (m, 13H), 4.05 (t, J=6.6 Hz, 2H), 5.26~5.47 (m, 4H), MS (FAB, POS): 877 (M+1), 859, 634, 596, 360 (FAB, NEG): 875 (M-1), 873, 831, 613, 534, 359, 305, 279

EXAMPLE 10

The dermatologic preparations of the present invention comprising 10% of each of the amide derivatives of the present invention listed in Table and 90% of squalane were prepared. Then the transepidermal water loss and percutaneous absorption of each of the dermatologic preparations were evaluated in the same manner as those described in Example 4. For comparison, a comparative dermatologic preparation comprising squalane alone was also evaluated. Table 4 summarizes the results.

TABLE 4

|  | Amide derivative | Transepidermal water loss | Percutaneous absorption |
|---|---|---|---|
| Product of Invention | compound of Ex. 6 (II-Aa) | 26.7 ± 7.3 | 124 ± 36.2 |
|  | compound of Ex. 7 (II-Ab) | 28.0 ± 8.4 | 516 ± 172 |
|  | compound of Ex. 8 (II-Ba) | 12.4 ± 3.2 | 779 ± 76.6 |
|  | compound of Ex. 9 (II-Ca) | 14.2 ± 4.2 | 340 ± 122 |
| Comparison | squalane alone | 35.8 ± 9.6 | 1220 ± 240 |

EXAMPLE 11

By using each of the amide derivatives of the present invention, the dermatologic preparations of the present invention as specified in Table 5 (emulsion cosmetic) were prepared. The effect of each product on improving skin chapping was evaluated in the same manner as the one described in Example 5. For comparison, a dermatologic preparation free from any amide derivative of the present invention (comparative product) was evaluated in the same manner. Table 5 summarizes the results.

TABLE 5

| (% by weight) | Invention products | Comparative product |
|---|---|---|
| methyl-branched isostearyl glyceryl ether | 2.0 | 2.0 |
| 2-octyldodecyl myristate | 10.0 | 10.0 |
| vaseline | 3.0 | 3.0 |
| squalane | 5.0 | 5.0 |
| tocopherol acetate | 0.5 | 0.5 |
| amide derivative (refer to Table 6) | 1.0 | — |
| water | the balance | the balance |

TABLE 6

|  | Amide derivative | Transepidermal water loss | Skin chapping score |
|---|---|---|---|
| Invention product | compound of Ex. 6 (II-Aa) | 25.4 ± 7.8 | 1.3 ± 0.3 |
|  | compound of Ex. 7 (II-Ab) | 22.8 ± 6.3 | 1.2 ± 0.4 |
|  | compound of Ex. 8 (II-Ba) | 12.1 ± 4.2 | 0.8 ± 0.3 |
|  | compound of Ex. 9 (II-Ca) | 12.3 ± 4.3 | 0.9 ± 0.3 |
| Comparative product | — | 28.6 ± 9.8 | 2.4 ± 0.7 |

What is claimed is:

1. An amide derivative represented by the following formula (II):

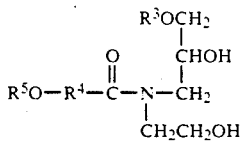 (II)

wherein $R^3$ represents a straight-chain or branched, saturated or unsaturated hydrocarbon group carrying 10 to 40 carbon atoms; $R^4$ represents a straight-chain or branched hydrocarbon group carrying 3 to 39 carbon atoms; and $R^5$ represents a hydrogen atom, a straight-chain or branched, saturated or unsaturated hydrocarbon group carrying 10 to 40 carbon atoms or an acyl group.

2. A dermatologic preparation comprising as an active ingredient an amide derivative as claimed in claim 1, in an amount of 0.01-50% by weight, relative to the total preparation, together with a suitable dermatologic base.

3. A dermatologic preparation comprising as an active ingredient an effective amount of an amide derivative as claimed in claim 1, together with a suitable dermatologic base.

4. The amide derivative according to claim 1, which is a member selected from the group consisting of
N-(2-hydroxy-3-hexadecyloxypropyl)-N-2-hydroxyethyl-triacontanamide;
N-(2-hydroxy-3-dotriacontyloxypropyl)-N-2-hydroxyethyltriacontanamide;
N-(2-hydroxy-3-dotriacontyloxypropyl)-N-2-hydroxyethylhexadecanamide;
N-(2-hydroxy-3-hexadecyloxypropyl)-N-2-hydroxyethyl-12-hydroxyoctadecanamide;
N-(2-hydroxy-3-hexadecyloxypropyl)-N-2-hydroxyethyl-16-hydroxyhexadecanamide;
N-(2-hydroxy-3-hexadecyloxypropyl-N-2-hydroxyethyl-16-(9Z,12Z-octadecadienyloxy)-hexadecanamide; and
N-(2-hydroxy-3-hexadecycloxypropyl)-N-2-hydroxyethyl-16-(9Z,12Z-octadecadienoyloxy)-hexadecanamide.

5. A dermatologic preparation which comprises as an active ingredient a dermatologically effective amount of an amide derivative according to claim 4, together with a suitable dermatologic base.

* * * * *